(12) United States Patent
Boschelli et al.

(10) Patent No.: US 7,919,625 B2
(45) Date of Patent: Apr. 5, 2011

(54) 4-ANILINO-3-QUINOLINECARBONITRILES FOR THE TREATMENT OF CHRONIC MYELOGENOUS LEUKEMIA (CML)

(75) Inventors: Frank Boschelli, New City, NY (US); Jennifer M. Golas, West Milford, NJ (US); Kim T. Arndt, Towaco, NJ (US)

(73) Assignee: Wyeth LLC, Madison, NJ (US)

( * ) Notice: Subject to any disclaimer, the term of this patent is extended or adjusted under 35 U.S.C. 154(b) by 403 days.

(21) Appl. No.: 12/139,834

(22) Filed: Jun. 16, 2008

(65) Prior Publication Data

US 2010/0029677 A1    Feb. 4, 2010

Related U.S. Application Data

(63) Continuation of application No. 10/980,097, filed on Nov. 3, 2004, now Pat. No. 7,417,148.

(60) Provisional application No. 60/517,819, filed on Nov. 6, 2003.

(51) Int. Cl.
    *C07D 215/38* (2006.01)
(52) U.S. Cl. .................. 546/159; 546/157; 514/313
(58) Field of Classification Search .................. 546/159, 546/157; 514/313
    See application file for complete search history.

(56) References Cited

U.S. PATENT DOCUMENTS

| 6,002,008 A | 12/1999 | Wissner et al. |
| 6,780,996 B2 | 8/2004 | Boschelli et al. |
| 7,417,148 B2 * | 8/2008 | Boschelli et al. ............ 546/159 |

FOREIGN PATENT DOCUMENTS

| WO | WO 03/093241 A1 | 11/2003 |
| WO | WO 2004/075898 A1 | 9/2004 |

OTHER PUBLICATIONS

Boschelli, J Med Chem, vol. 44, pp. 822-833, 2001.*
Boschelli, J Med Chem, vol. 44, pp. 3965-3977, 2001.*
Boschelli, D.H.; et al.; J. Med. Chem. 44:3965-3911 (2001).
Boschelli, D.H.; et al.; J. Med. Chem. 47:1599-1601 (2004).
Boschelli, D.H., et al.; J. Med. Chem. 44:822-833 (2001).
Boschelli, D.H., et al.; Bioorganic & Medicinal Chemistry Letters 13:3797-3800 (2003).
Golas, J.M.; et al.; Cancer Research 63:375-381 (Jan. 15, 2003).
Ye, F.; 221st National Meeting of the American Chemical Society, San Diego (Apr. 2001).
Registry compound No. 220127-57-1, Mar. 3, 1999.
Huy, et al., "Requirement of Src kinases Lyn, Hck and Fgr for BCR-ABL1-induced B-lymphoblastic leukemia but not chronic myeloid leukemia", Nature Genetics, vol. 36, (2004) pp. 453-461.
Berger, D., et al.; Substituted 4-Anillno-7-phenyl-3-quinolinecarbonitriles as Src Kinase inhibitors; Bioorg. Med. Chem. Lett 12:2989-2992 (2002).

* cited by examiner

*Primary Examiner* — D. Margaret Seaman
(74) *Attorney, Agent, or Firm* — David Rubin; Jeffrey H. Tidwell

(57) ABSTRACT

Compounds of the formula:

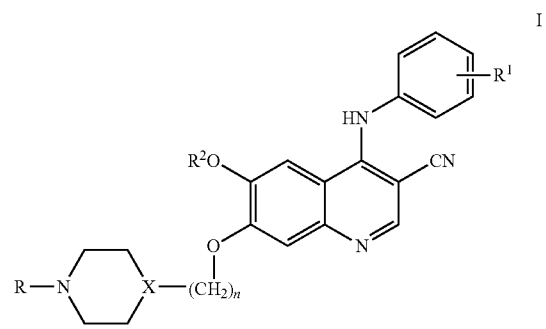

wherein:
n is an integer from 1-3;
X is N, CH, provided that when X is N, n is 2 or 3;
R is alkyl of 1 to 3 carbon atoms;
$R^1$ is 2,4-diCl, 5-OMe; 2,4-diCl; 3,4,5-tri-OMe; 2-Cl, 5-OMe; 2-Me, 5-OMe; 2,4-di-Me; 2,4-diMe-5-OMe, 2,4-diCl, 5-OEt;
$R^2$ is alkyl of 1 to 2 carbon atoms, and pharmaceutically acceptable salts thereof.

1 Claim, No Drawings

SEQUENCE LISTING

```
<160> NUMBER OF SEQ ID NOS: 6

<210> SEQ ID NO 1
<211> LENGTH: 48
<212> TYPE: DNA
<213> ORGANISM: Artificial
<220> FEATURE:
<223> OTHER INFORMATION: primer for human c-Src

<400> SEQUENCE: 1
cgcctggcca acgtctgccc cacgtccaag ccgcagactc agggcctg          48

<210> SEQ ID NO 2
<211> LENGTH: 50
<212> TYPE: DNA
<213> ORGANISM: Artificial
<220> FEATURE:
<223> OTHER INFORMATION: primer for human c-Src

<400> SEQUENCE: 2
ccaacacaca agcagggagc agctgggcct gcaggtactc gaaggtgggc          50

<210> SEQ ID NO 3
<211> LENGTH: 26
<212> TYPE: DNA
<213> ORGANISM: Artificial
<220> FEATURE:
<223> OTHER INFORMATION: primer for human v-Src

<400> SEQUENCE: 3
gtgcctattg cctctccgtt tctgac          26

<210> SEQ ID NO 4
<211> LENGTH: 25
<212> TYPE: DNA
<213> ORGANISM: Artificial
<220> FEATURE:
<223> OTHER INFORMATION: primer for human v-Src

<400> SEQUENCE: 4
```

```
acgtggggca gacgttggcc aggcg                                     25

<210> SEQ ID NO 5
<211> LENGTH: 25
<212> TYPE: DNA
<213> ORGANISM: Artificial
<220> FEATURE:
<223> OTHER INFORMATION: primer for human v-Src

<400> SEQUENCE: 5
cagctgctcc ctgcttgtgt gttgg                                     25

<210> SEQ ID NO 6
<211> LENGTH: 40
<212> TYPE: DNA
<213> ORGANISM: Artificial
<220> FEATURE:
<223> OTHER INFORMATION: primer for human v-Src

<400> SEQUENCE: 6
atgaattctc tagaggaaga cgccatcata ttccaagcag                     40
```

4-ANILINO-3-QUINOLINECARBONITRILES FOR THE TREATMENT OF CHRONIC MYELOGENOUS LEUKEMIA (CML)

This application is a continuation application of copending application, application Ser. No. 10/980,097 filed Nov. 3, 2004 which claims priority from provisional application, Application No. 60/517,819 filed on Nov. 6, 2003. These applications are herein incorporated by reference in their entireties.

BACKGROUND OF THE INVENTION

Constitutive tyrosine kinase activity of Bcr-Abl promotes proliferation and survival of chronic myelogenous leukemia (CML) cells. Inhibition of Bcr-Abl tyrosine kinase activity or signaling proteins activated by Bcr-Abl in CML cells blocks proliferation and causes apoptotic cell death. The selective Abl kinase inhibitor, STI-571 (marketed as Gleevec), is toxic to CML cells in culture, causes regression of CML tumors in nude mice, and is currently used to treat CML patients.

Expression of Bcr-Abl in hematopoietic stem cells promotes transformation and acts early in leukemogenesis. Inhibition of this kinase with STI-571 effectively controls CML in the chronic phase of the disease but more advanced patients frequently progress on STI-571 therapy. These observations suggest that additional molecular changes that are not affected by STI-571 play a role in advanced disease. In vitro models of STI-571 resistance and clinical specimens from resistant patients demonstrated that overexpression of other kinases or activation of distinct signaling pathways is associated with Bcr-Abl independence. Inhibition of the tyrosine kinase activity of Bcr-Abl is an effective strategy for targeting CML as demonstrated by the clinical efficacy of STI-571. Other molecules, including Src family kinases, play a role in downstream signaling from Bcr-Abl, and as such, are potential therapeutic targets for the treatment of STI-571-resistant disease. Src family kinases including Lyn and Hck have been implicated in downstream signaling from Bcr-Abl.

Although the selective Abl kinase inhibitor STI-571 is efficacious and well tolerated by most patients in chronic-stage CML, patients in accelerated and blast crises stages of the disease tend to be less responsive. Consequently, there is a need for alternative agents that are effective in late-stage disease.

BRIEF SUMMARY OF THE INVENTION

In accordance with the present invention are provided compounds of the structural formula I:

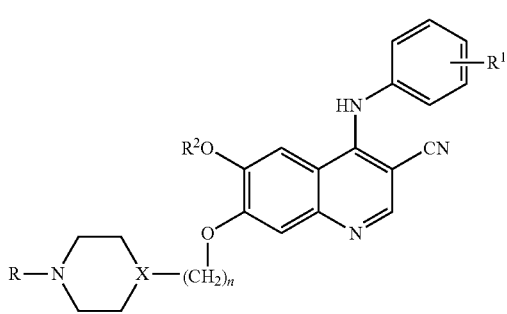

wherein:
n is an integer from 1-3;
X is N, CH, provided that when X is N, n is 2 or 3;
R is alkyl of 1 to 3 carbon atoms;
$R^1$ is 2,4-diCl, 5-OMe; 2,4-diCl; 3,4,5-tri-OMe; 2-Cl, 5-OMe; 2-Me, 5-OMe; 2,4-di-Me; 2,4-diMe-5-OMe, 2,4-diCl, 5-OEt;
$R^2$ is alkyl of 1 to 2 carbon atoms, and pharmaceutically acceptable salts thereof.

The compounds of this invention may be used for treating, preventing, or inhibiting CML. In a preferred embodiment the compounds are used as part of a pharmaceutical composition.

Specific compounds of the invention include:
4-[(2,4-Dichloro-5-methoxyphenyl)amino]-6-methoxy-7-[3-(4-methyl-1-piperazinyl)propoxy]-3-quinolinecarbonitrile;
4-[(2,4-Dichloro-5-methoxyphenyl)amino]-7-[3-(4-ethyl-1-piperazinyl)propoxy]-6-methoxy-3-quinolinecarbonitrile;
4-[(2,4-Dichloro-5-methoxyphenyl)amino]-6-methoxy-7-[2-(4-methyl-1-piperazinyl)ethoxy]-3-quinolinecarbonitrile;
4-[(2,4-Dichloro-5-methoxyphenyl)amino]-7-[2-(4-ethyl-1-piperazinyl)ethoxy]-6-methoxy-3-quinolinecarbonitrile;
4-[(2,4-Dichloro-5-methoxyphenyl)amino]-6-methoxy-7-[(1-methylpiperidin-4-yl)methoxy]-3-quinolinecarbonitrile;
4-[(2,4-Dichloro-5-methoxyphenyl)amino]-6-methoxy-7-[2-(1-methylpiperidin-4-yl)ethoxy]-3-quinolinecarbonitrile;
4-[(2,4-Dichloro-5-methoxyphenyl)amino]-6-methoxy-7-[3-(1-methylpiperidin-4-yl)propoxy]quinoline-3-carbonitrile;
4-[(2,4-Dichloro-5-methoxyphenyl)amino]-7-[(1-ethylpiperidin-4-yl)methoxy]-6-methoxyquinoline-3-carbonitrile;
4-[(2,4-Dichloro-5-methoxyphenyl)amino]-6-ethoxy-7-[3-(4-methylpiperazin-1-yl)propoxy]quinoline-3-carbonitrile;
4-[(2,4-Dichloro-5-methoxyphenyl)amino]-6-ethoxy-7-[(1-methylpiperidin-4-yl)methoxy]quinoline-3-carbonitrile;
4-[(2,4-Dichloro-5-methoxyphenyl)amino]-6-ethoxy-7-[3-(4-ethylpiperazin-1-yl)propoxy]quinoline-3-carbonitrile;
4-[(2,4-Dichloro-5-methoxyphenyl)amino]-6-ethoxy-7-[3-(1-methyl piperidin-4-yl)propoxy]quinoline-3-carbonitrile;
4-[(2,4-Dichloro-5-methoxyphenyl)amino]-6-ethoxy-7-[2-(4-methyl-1-piperazinyl)ethoxy]quinoline-3-carbonitrile;
4-[(2,4-Dichloro-5-methoxyphenyl)amino]-6-ethoxy-7-[2-(1-methylpiperidin-4-yl)ethoxy]quinoline-3-carbonitrile;
4-[(2,4-Dichloro-5-methoxyphenyl)amino]-6-methoxy-7-[3-(4-propyl-1-piperazinyl)propoxy]-3-quinolinecarbonitrile;
4-[(2,4-dichlorophenyl)amino]-6-methoxy-7-[(1-methylpiperidin-4-yl)methoxy]-3-quinolinecarbonitrile;
6-methoxy-7-[(1-methylpiperidin-4-yl)methoxy]-4-[(3,4,5-trimethoxyphenyl)amino]quinoline-3-carbonitrile;
4-[(2-chloro-5-methoxyphenyl)amino]-6-methoxy-7-[(1-methylpiperidin-4-yl)methoxy]quinoline-3-carbonitrile;
6-methoxy-4-[(5-methoxy-2-methylphenyl)amino]-7-[(1-methylpiperidin-4-yl)methoxy]quinoline-3-carbonitrile;
4-[(2,4-dimethylphenyl)amino]-6-methoxy-7-[(1-methylpiperidin-4-yl)methoxy]quinoline-3-carbonitrile;
6-methoxy-4-[(5-methoxy-2,4-dimethylphenyl)amino]-7-[(1-methylpiperidin-4-yl)methoxy]quinoline-3-carbonitrile;
4-[(2,4-dichloro-5-ethoxyphenyl)amino]-6-methoxy-7-[(1-methylpiperidin-4-yl)methoxy]quinoline-3-carbonitrile;
and pharmaceutically acceptable salts thereof.

The following experimental details are set forth to aid in an understanding of the invention, and are not intended, and should not be construed, to limit in any way the invention set forth in the claims that follow thereafter.

DETAILED DESCRIPTION OF THE INVENTION

In accordance with the present invention are provided compounds of the structural formula I:

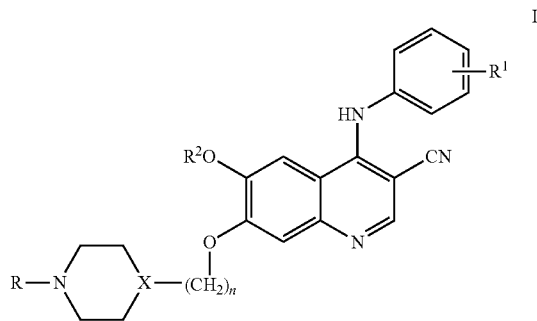

wherein:
n is an integer from 1-3;
X is N, CH, provided that when X is N, n is 2 or 3;
R is alkyl of 1 to 3 carbon atoms;
$R^1$ is 2,4-diCl, 5-OMe; 2,4-diCl; 3,4,5-tri-OMe; 2-Cl, 5-OMe; 2-Me, 5-OMe; 2,4-di-Me; 2,4-diMe-5-OMe, 2,4-diCl, 5-OEt;
$R^2$ is alkyl of 1 to 2 carbon atoms, and pharmaceutically acceptable salts thereof.

The compounds of this invention may be used for treating, preventing, or inhibiting CML. In a preferred embodiment the compounds are used as part of a pharmaceutical composition.

Pharmaceutically acceptable salts are those derived from such organic and inorganic acids as: acetic, lactic, carboxylic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In a preferred embodiment, a straight chain or branched chain alkyl has 3 or fewer carbon atoms in its backbone.

The compounds may be provided orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 300 mg of a compound of the invention and preferably from 2 to 100 mg. In another embodiment the unit dosage forms contain 50 to 150 mg of a compound of the present invention. The compounds of the present invention can be administered orally. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The compound of the present invention may be delivered locally via a capsule that allows a sustained release of the compound over a period of time. Controlled or sustained release compositions include formulation in lipophilic depots (for example, fatty acids, waxes, oils).

The present invention further provides a compound of the invention for use as an active therapeutic substance for treating, preventing, or inhibiting CML.

The present invention further provides a method of treating CML in humans, which comprises administering to the infected individual an effective amount of a compound or a pharmaceutical composition of the invention. The dose provided to a patient will vary depending upon what is being administered, the purpose of the administration, the manner of administration, and the like. A "therapeutically effective amount" is an amount sufficient to cure or ameliorate symptoms of CML.

The compounds of this may be delivered alone or in combination with other compounds used to treat CML. Such compounds include but are not limited to GLEEVEC, hydroxyurea, IFN-α, cytotoxic agents, 17-(Allylamino)-17-demethoxygeldanamycin or derivatives thereof, or wortmannin.

The compounds of this invention were prepared from: (a) commercially available starting materials (b) known starting materials which can be prepared as described in literature procedures or (c) new intermediates described in the schemes and experimental procedures herein. Compounds included in this invention can be prepared according to the synthesis routes disclosed in U.S. Pat. Nos. 6,002,008, and 6,780,996, such procedures are hereby incorporated by reference.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. When not specified, order of synthetic steps, choice of protecting groups and deprotection conditions will be readily apparent to those skilled in the art. In addition, in some instances, substituents on the starting materials may be incompatible with certain reaction conditions. Restrictions pertinent to given substituents will be apparent to one skilled in the art. Reactions were run under inert atmospheres where appropriate.

The preparation of compounds of Formula I have been reported in the literature, [Boschelli, D. H., et. al., J. Med. Chem., 44, 3965 (2001)], Boschelli, D. H., et al., J. Med. Chem., 44, 822 (2001), Boschelli, D. H., et al., Bioorg. Med. Chem. Lett., 13, 3797 (2003), Boschelli, D. H., et. al., J. Med. Chem., 47, 1599 (2004), and Ye, F. et. al., 221*th National Meeting of the American Chemical Society*, San Diego, Calif. (April, 2001)].

This invention will be more fully described in conjunction with the following specific examples which are not to be construed as limiting the scope of this invention.

Materials and Methods:
Src kinase assay, homogeneous solution-based assay (Lance format)
Kinase Buffer:
50 mM Hepes pH 7.5
10 mM MgCl2
20 ug/ml BSA
0.001% Brij-35
(Prepare 2× kinase buffer for convenience:
100 mM Hepes, 20 mM MgCl2, add fresh 40 ug/ml BSA and 0.002% Brij)
Quench Buffer (to be added straight, 1:1, to reaction mix)
50 mM Hepes pH 7.5
60 mM EDTA
20 ug/ml BSA
Lance Detection Buffer and Plate Blocker:
50 mM Hepes pH 7.5
20 ug/ml BSA Add EU-antibody PT66 (Perkin-Elmer) (1 nM) and APC-streptavidin (Perkin-Elmer) (4 ug/ml) for 100 ul/well just prior to using (add 100 ul to 50 ul rxn/50 ul quench for 200 ul final). 5×ATP=500 uM in water.

1. Rinse 96 well plate with 200 ul PBS. Preincubate 96 well black plate with 200 ul of 50 mM Hepes pH 7.5 with 20 ug/ml BSA for 10 minutes (lance detection buffer).
2. Kinase reaction takes place in a total volume of 50 ul kinase buffer in the 96 well plate. Use biotinylated substrate peptide at a final concentration of 2 uM, and src from Panvera at 5 ng per 50 ul reaction. The reaction is initiated by addition of 10 ul 5×ATP (final concentration 1×=100 uM) and carried out for 50 min @ 37° C. (per rxn: 25 ul 2× kinase buffer, 10 ul water, 5 ul diluted compound-10% DMSO/10 mM Hepes).
3. To stop kinase reaction add 50 ul of Quench buffer and shake for 30 s.
4. Add 100 ul of Lance detection buffer containing EU antibody and APC-strep. Add EU-antibody PT66 (1 nM) and APC-streptavadin (4 ug/ml) for 100 ul/well just prior to using (add 100 ul to 50 ul rxn/50 ul quench for 200 ul final).

Incubate for 1 h @ room temp in the dark. Read Plate using the standard Lance protocol on the Wallac Victor.

Src Kinase Assay

Inhibitors of Src (partially purified enzyme preparation purchased from Upstate Biotechnologies, Lake Placid, N.Y.) tyrosine kinase activity are analyzed in an ELISA format. The Boehringer Mannheim Tyrosine Kinase Assay Kit (Roche Diagnostics, Basel, Switzerland) with a cdc2 substrate peptide containing Tyr15 is used for the assay. Horseradish Peroxidase (HRP)-conjugated anti-phosphotyrosine is used to detect phosphorylated peptide via a color reaction.

Reaction conditions: Five microliter aliquots of each compound prepared fresh at the time of the assay are added as a solution in 10 mM HEPES pH 7.5, 10% DMSO to the reaction well. Thirty-five microliters of reaction mix containing Src, buffer and peptide/bovine serum albumin mix are added to the compound wells and incubated at 30° C. for 10 minutes (reaction buffer: 50 mM TrisHCl pH 7.5, 10 mM $MgCl_2$, 0.1 mM EGTA, 0.5 mM $Na_3VO_4$). The reaction is started by addition of 10 microliters of ATP (500 μM), incubated at 30° C. for 1 hour, and stopped by addition of 20 microliters of 0.5M EDTA. The reaction mixture with the phosphorylated peptide is then transferred to a streptavidin-coated microtiter plate and allowed to bind for 20 minutes. Unbound peptide and reaction mixture is decanted and the plate is washed with PBS six times. HRP-conjugated phosphotyrosine antibody supplied in the kit is incubated with the plate for one hour, then decanted. The plate is again washed with PBS six times. Substrate is added and absorbance at 405 nm is measured.

Alternatively, the assay performed essentially as described except a Delfia format (Perkin-Elmer) is used and Europium-conjugated phosphotyrosine antibody was used instead of HRP-conjugated phosphotyrosine antibody, Pierce Superblock was used in place of bovine serum albumin and 6 washes were employed after the kinase reaction and antibody binding. Europium fluorescence was used to monitor the extent of reaction.

Activity is determined as % inhibition as calculated by the formula: $(1-Abs/Abs(max))\times 100 = \%$ inhibition. Where multiple concentrations of the test agent are used, an $IC_{50}$ (concentration which gives 50% inhibition) can be determined. As shown in Table 2, compounds of the invention inhibit src kinase in vitro.

Homogeneous solution-based Abl kinase assay: Abl kinase activity was measured in a homogeneous assay format (Lance) where luminescence of a donor-acceptor complex bound to peptide phosphorylated by the kinase is measured in solution.

Biotinylated substrate peptide: Biotin-NH-KEEE-AIYAAPFAKKK-COOH (Synpep)

Kinase Buffer: 50 mM Hepes pH 7.5; 10 mM $MgCl_2$; 20 ug/ml BSA; 0.001% Brij-35; prepared as a 2× concentrate for convenience: 100 mM Hepes, 20 mM $MgCl_2$, add fresh 40 ug/ml BSA and 0.002% Brij-35

Quench Buffer to be added in equal proportions to the reaction mix: 50 mM Hepes pH 7.5; 60 mM EDTA; 20 μg/ml BSA Lance Detection Buffer and plate blocker: 50 mM Hepes pH 7.5; 20 µg/ml BSA Detection Mix: Antibody-APC reagent in Lance buffer to be added in equal proportions to the rxn mix/quench mix. Add 100 µL/well Lance detection buffer containing Eu-antibody PT66 (Perkin Elmer, AD0068; 1 nM final concentration in Lance detection buffer) and Streptavidin Surelight-APC (Perkin Elmer, CR130-100; 4 µg/mL final concentration in Lance detection buffer).

5×ATP=500 µM in water

Method:
1. Rinse 96 well plate with 200 µl PBS. Incubate 96 well black plate (Thermo LabSystems MicroFluor 2 black U-bottom microtiter plate; # 7205) with 200 µL of Lance detection buffer for 10 minutes.
2. Kinase reaction consists of a total volume of 50 µL kinase buffer/reaction in each well of a 96 well plate. Substrate peptide is present at a final concentration of 2 µM, and c-Abl from Panvera (c-Abl P3049) is included at 2.5 ng per 50 µL reaction. (per rxn: 25 µL 2× kinase buffer, 10 µL water, 5 µL diluted compound-10% DMSO/10 mM Hepes, pH 7.5). The reaction is initiated by addition of 10 µL 5×ATP (final concentration 1×=100 µM) and continued for 30 min @ 27° C.
3. Add 50 µL of Quench buffer to stop the kinase reaction.
4. Add 100 µL of Detection Mix.
5. Incubate for 30 min @ room temp in the dark. Measure luminescence at 665 nm on the Wallac Victor.

ANALYSIS OF RESULTS: % Inhibition=($Cpm$(sample)−$Bkg$)/($Cpm$(control)−$Bkg$))×100

The LSW data analysis plug-in for Excel (Model 63) is used to calculate IC50 values (y=Bmax/(1+(x/IC50)) Hyperbolic inhibition curve, Bmax to 0 (IC50).

These transformed Rat2 fibroblasts are used for the measurement of src dependent suspension growth.

Ultra-low cluster plates (Corning Costar, Acton, Mass.) are seeded with 10,000 cells per well on day 1. Alternatively, Ultra-low cluster plates (Costar 3474) treated with Sigmacote (Sigma, St. Louis, Mo.), rinsed with 70% ethanol, after drying in the hood, are seeded with 5000 cells. Compound is added in serial two-fold dilutions from 10 micromolar to 0.009 micromolar on day 2 and MTS reagent (Promega, Madison, Wis.) is added on day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition=(Abs 490 nm sample−blank)/(Abs 490 nm no cmpd control−blank)×100%.

Alternatively relative cell numbers were determined by the CellTiter-Glo™ (Promega) method. All procedures were identical except that cell number was reduced to 1000 cells/well and CellTiter-Glo reagent was added instead of MTS reagent, with luminescence as the readout.

Anchorage Independent Src-Transformed Fibroblast Proliferation Assay

Rat2 fibroblasts stably transformed with a plasmid containing a CMV promoter controlled v-Src/HU c-Src fusion gene in which the catalytic domain of human c-Src gene as follows:

Cloning and plasmid constructions: the Prague C v-Src gene from pSrcHis (Wendler and Boschelli, Oncogene 4: 231-236; 1989) was excised with NcoI and BamHI, treated with T4 DNA polymerase, and cloned into the RI site of pTRE (Clontech) that had been rendered flush by treatment with T4 DNA polymerase. The PRC v-Src::hu c-Src fusion was created by replacing the Bgl2-Xbal fragment encoding the carboxyl terminal ~250 amino acids of v-Src with the Bgl2-Xbal fragment containing the v-Src::huc-Src fusion fragment (below). A partial clone of human c-Src was amplified from a breast cDNA library (InVitrogen) using the oligonucleotide pair 5'-CGCCTGGCCAACGTCTGC-CCCACGTCCAAGCCGCAGACTCAGGGCCTG-3' (SEQ. ID NO: 1) and 5'-CCAACACACAAGCAGGGAG-CAGCTGGGCCTGCAGGTACTCGAAGGTGGGC-3' (SEQ. ID NO: 2) and cloned into pCRScript (Stratagene). The catalytic domain of human c-Src in this clone was amplified with these oligonucleotides (fuses v-src nucleotide 734 to human c-Src nucleotide 742 and human c-Src nucleotide 1551 to v-src nucleotide 1543 in the v-Src and human c-Src ORFs). Two v-Src sequences were amplified by PCR (198 base pair v-src 5' fragment: 5'-GTGCCTATTGCCTCTC-CGTTTCTGAC-3' (SEQ. ID NO: 3)(primer 1) to 5'-ACGTGGGGCAGACGTTGGCCAGGCG-3') (SEQ. ID NO: 4)(252 base pair 3' v-src fragment, 5'-CAGCTGCTC-CCTGCTTGTGTGTTGG-3' (SEQ. ID NO: 5) (residues 1543-1567 in v-src ORF) to 5'-ATGAATTCTCTAGAG-GAAGACGCCATCATATTCCAAGCAG-3' (SEQ. ID NO: 6) (residues 1769-1794 from v-src ATG with Xbal and EcoRI restriction sites added (primer 4)). Primers 1 and 4 were used to generate a three-fragment PCR amplification and fusion of the v-Src: human c-Src fusion fragment and the 5' and 3' fragments amplified from the Prague C v-Src gene and 3' untranslated region from Rous sarcoma virus. This reaction creates an in-frame v-Src::human c-Src gene fusion (amino acid residue V244 of v-Src to C248 of human c-Src on the amino terminal side and A517 of human c-Src to Q515 of v-Src). This gene fusion fragment encodes the carboxyl terminal one-third of the v-Src $SH_2$ domain and $SH_2$-catalytic domain linker fused to the human c-Src catalytic domain flanked by the v-Src carboxyl-terminal tail. A naturally occurring Bgl2 site near the 5' end of the fusion fragment and the engineered Xbal site at the 3' end of the fragment were used to excise fragment for creation of the full-length v-Src::human c-Src fusion gene as described above. The integrity of the constructs was confirmed by DNA sequencing. Similar methods were used to clone this gene into other expression plasmids such as pIRES (Clontech) for use in these studies.

Abl Kinase Assay.

Bacterially expressed Abl kinase was obtained from New England Biolabs. Kinase assays were performed in a DELFIA solid phase europium-based detection assay format (Perkin-Elmer). The peptide was as described in Dorsey et al. (46). Biotinylated peptide (2 µM) was bound to streptavidin coated microtitration plates (Perkin Elmer CC11-205) for 1.5 hour in 1 micrograms/ml ovalbumin in Phospate Buffered Saline (PBS). The plates were washed for 1 hour with PBS/ 0.1% Tween 80, followed by a PBS wash. The kinase reaction was incubated for 1 hour at 30° C. Abl kinase (10 units, NEB P6050L) was mixed with 50 mM Tris-HCl, pH 7.5, 10 mM $MgCl_2$, 80 µM EGTA, 100 µM ATP, 0.5 mM $Na_3VO_4$, 1% DMSO, 1 mM HEPES (pH 7) and 200 µg/ml ovalbumin. The reaction was stopped with EDTA at a final concentration of 50 mM. The DELFIA wash protocol suggested by the manufacturer (Perkin Elmer) was modified by extending wash times to reduce background. The reaction was monitored with Eu-labeled phosphotyrosine antibody (Perkin Elmer AD0040) and DELFIA Enhancement solution (Perkin Elmer 1244-105) according to manufacturer specifications.

Determination of Anti-Proliferative Activity of Compounds of Abl-Dependent Cells A. Inhibition of v-Abl-dependent proliferation. Rat 2 cells infected with Abl-murine leukemia virus were grown and treated as described for the Src cell assay. All measurements were identical except for the cell type that Cell-Titer Glo (Promega) was used to monitor relative cell number. In this case, the reagent was used as recommended by the manufacturer and luminescence was measured on a Wallac Victor plate reader.

B. Inhibition of CML cell proliferation. KU812 and K562 cells were grown in RPMI1640 medium supplemented with 10% fetal calf serum and glutamine with 50 µg/ml gentamicin. Cells were plated at 1000-2000 cells per well on Day 0. On Day 1, compound was added such that the final DMSO concentration was no greater than 0.1%. On Day 4, Cell-Titer Glo was added according to manufacturer specifications and luminescence was determined on a Wallac Victor plate reader.

Results of these experiments are presented in Tables 1, 2 and 3 below.

Example 1

4-[(2,4-Dichloro-5-methoxyphenyl)amino]-6-methoxy-7-[3-(4-methyl-1-piperazinyl)propoxy]-3-quinolinecarbonitrile mp 116-120° C.; MS (ES) m/z 530.2, 532.2 (M+1);

Example 2

4-[(2,4-Dichloro-5-methoxyphenyl)amino]-7-[3-(4-ethyl-1-piperazinyl)propoxy]-6-methoxy-3-quinolinecarbonitrile mp 102-104° C.; MS (ES) m/z 544.3, 546.4 (M+1);

Example 3

4-[(2,4-Dichloro-5-methoxyphenyl)amino]-6-methoxy-7-[2-(4-methyl-1-piperazinyl)ethoxy]-3-quinolinecarbonitrile mp 165-167° C.; MS (ES) m/z 516.0, 518.2 (M+1);

Example 4

4-[(2,4-Dichloro-5-methoxyphenyl)amino]-7-[2-(4-ethyl-1-piperazinyl)ethoxy]-6-methoxy-3-quinolinecarbonitrile mp 101-105° C.; MS (ES) m/z 530.4, 532.4 (M+1);

Example 5

4-[(2,4-Dichloro-5-methoxyphenyl)amino]-6-methoxy-7-[(1-methylpiperidin-4-yl)methoxy]-3-quinolinecarbonitrile mp 200-202° C., MS 501.3 (M+H)$^+$, Analysis for $C_{25}H_{26}Cl_2N_4O_3$-0.8$H_2O$, Calcd: C, 58.21; H, 5.39; N, 10.86, Found: C, 58.19; H, 5.23; N, 10.67;

Example 6

4-[(2,4-Dichloro-5-methoxyphenyl)amino]-6-methoxy-7-[2-(1-methylpiperidin-4-yl)ethoxy]-3-quinolinecarbonitrile mp 190-191° C., MS 515.19 (M+H)$^+$, Analysis for $C_{26}H_{28}Cl_2N_4O_3$-1.0$H_2O$, Calcd: C, 58.53; H, 5.67; N, 10.50, Found: C, 58.65; H, 5.57; N, 10.34

Example 7

4-[(2,4-Dichloro-5-methoxyphenyl)amino]-6-methoxy-7-[3-(1-methylpiperidin-4-yl)propoxy]quinoline-3-carbonitrile MP 144-145° C.; Mass spec. 529.2 (ES+);

Example 8

4-[(2,4-Dichloro-5-methoxyphenyl)amino]-7-[(1-ethylpiperidin-4-yl)methoxy]-6-methoxyquinoline-3-carbonitrile MP 192-195° C.; Mass spec. 515.2 (ES+);

Example 9

4-[(2,4-Dichloro-5-methoxyphenyl)amino]-6-ethoxy-7-[3-(4-methylpiperazin-1-yl)propoxy]quinoline-3-carbonitrile mp 137-138° C., MS 542.0 (M−H)$^−$, Analysis for $C_{27}H_{31}Cl_2N_5O_3$-0.6$H_2O$, Calcd: C, 58.40; H, 5.84; N, 12.61, Found: C, 58.31; H, 5.71; N, 12.43;

Example 10

4-[(2,4-Dichloro-5-methoxyphenyl)amino]-6-ethoxy-7-[(1-methylpiperidin-4-yl)methoxy]quinoline-3-carbonitrile mp 182-186° C., MS 513.0 (M−H)$^−$, Analysis for $C_{26}H_{28}Cl_2N_4O_3$-1.4$H_2O$ Calcd: C, 57.76; H, 5.74; N, 10.36, Found: C, 57.65; H, 5.43; N, 10.15;

Example 11

4-[(2,4-Dichloro-5-methoxyphenyl)amino]-6-ethoxy-7-[3-(4-ethylpiperazin-1-yl)propoxy]quinoline-3-carbonitrile mp 127-130° C., MS 558.3 (M+H)$^+$, Analysis for $C_{28}H_{33}Cl_2N_5O_3$-1.5$H_2O$, Calcd: C, 57.44; H, 6.20; N, 11.96, Found: C, 57.44; H, 6.24; N, 11.79;

Example 12

4-[(2,4-Dichloro-5-methoxyphenyl)amino]-6-ethoxy-7-[3-(1-methylpiperidin-4-yl)propoxy]quinoline-3-carbonitrile mp 148-151° C.

MS 543.2 (M+H)+, Analysis for $C_{28}H_{32}Cl_2N_4O_3 \cdot 1.8H_2O$, Calcd: C, 58.39; H, 6.23; N, 9.73, Found: C, 58.40; H, 6.16; N, 9.64;

Example 13

4-[(2,4-Dichloro-5-methoxyphenyl)amino]-6-ethoxy-7-[2-(4-methyl-1-piperazinyl)ethoxy]quinoline-3-carbonitrile mp 141-143° C., MS 530.2 (M+H)+, Analysis for $C_{26}H_{29}Cl_2N_5O_3$, Calcd: C, 58.87; H, 5.51; N, 13.20, Found: C, 58.48; H, 5.45; N, 12.95;

Example 14

4-[(2,4-Dichloro-5-methoxyphenyl)amino]-6-ethoxy-7-[2-(1-methylpiperidin-4-yl)ethoxy]quinoline-3-carbonitrile mp 174-176° C., MS 529.1 (M+H)+, Analysis for $C_{27}H_{30}Cl_2N_4O_3$, Calcd: C, 61.25; H, 5.71; N, 10.58, Found: C, 61.40; H, 5.84; N, 10.35;

Example 15

4-[(2,4-Dichloro-5-methoxyphenyl)amino]-6-methoxy-7-[3-(4-propyl-1-piperazinyl)propoxy]-3-quinolinecarbonitrile mp 97-101° C.; MS (ES) m/z 558.2, 560.2 (M+1);

Example 16

4-[(2,4-dichlorophenyl)amino]-6-methoxy-7-[(1-methylpiperidin-4-yl)methoxy]-3-quinolinecarbonitrile mp 224-225° C., MS 469.0 (ES−);

Example 17

6-methoxy-7-[(1-methylpiperidin-4-yl)methoxy]-4-[(3,4,5-trimethoxyphenyl)amino]quinoline-3-carbonitrile mp>245° C.; HRMS (M+H)+ calculated 493.24455, found 493.24311;

Example 18

4-[(2-chloro-5-methoxyphenyl)amino]-6-methoxy-7-[(1-methylpiperidin-4-yl)methoxy]quinoline-3-carbonitrile mp 106-108° C., MS 467.2 (ES+);

Example 19

6-methoxy-4-[(5-methoxy-2-methylphenyl)amino]-7-[(1-methylpiperidin-4-yl)methoxy]quinoline-3-carbonitrile mp>250° C., MS 445.2 (ES−);

Example 20

4-[(2,4-dimethylphenyl)amino]-6-methoxy-7-[(1-methylpiperidin-4-yl)methoxy]quinoline-3-carbonitrile mp 190-191° C., MS 429.2 (ES−);

Example 21

6-methoxy-4-[(5-methoxy-2,4-dimethylphenyl)amino]-7-[(1-methylpiperidin-4-yl)methoxy]quinoline-3-carbonitrile mp 160-162° C., MS 461.3 (ES+);

Example 22

4-[(2,4-dichloro-5-ethoxyphenyl)amino]-6-methoxy-7-[(1-methylpiperidin-4-yl)methoxy]quinoline-3-carbonitrile

TABLE 1

| ex | c-Abl Enzyme[a] $IC_{50}$ nM | v-Abl cells $IC_{50}$ nM | K562 $IC_{50}$ nM | KU812 $IC_{50}$ nM |
|---|---|---|---|---|
| 1 | 1.1 (n = 2) | 76 (n = 6) | 20 (n = 19) | 5.0 (n = 12) |
| 3 | not tested | 440 | 48 (n = 2) | not tested |
| 5 | 2.9 (n = 2) | 617 | 39 (n = 3) | 13.4 (n = 4) |
| 6 | 2.9 (n = 2) | 458 | 41 | 14.0 |
| 7 | 0.8 (n = 2) | 185 | 18 (n = 4) | 5.8 (n = 2) |
| 16 | 16.0 | | | |
| 17 | 12.0 | | | |
| 18 | 3.5 | | | |
| 19 | 8.3 | | | |
| 20 | 38.0 | | | |
| 21 | 8.3 | | | |

TABLE 2

Tested in the Src enzyme assay, Examples 1-15 ELISA format, Examples 20-25 LANCE format

| EXAMPLE | Src enzyme $IC_{50}$ nM | Src cells $IC_{50}$ nM |
|---|---|---|
| 1 | 1.2 | 100 |
| 2 | 0.77 | 130 |
| 3 | 4.0 | 380 |
| 4 | 3.6 | 600 |
| 5 | 2.0 | 320 |
| 6 | 1.9 | 210 |
| 7 | 1.4 | 100 |
| 8 | 2.1 | 170 |
| 9 | 1.2 | 86 |
| 10 | 2.1 | 176 |
| 11 | 0.85 | 160 |
| 12 | 1.4 | 96 |
| 13 | 1.5 | 146 |
| 14 | 1.9 | 267 |
| 15 | 1.1 | 160 |
| 16 | 6.6 | 1400 |

TABLE 2-continued

Tested in the Src enzyme assay, Examples 1-15
ELISA format, Examples 20-25 LANCE format

| EXAMPLE | Src enzyme IC$_{50}$ nM | Src cells IC$_{50}$ nM |
|---|---|---|
| 17 | 8.3 | 1600 |
| 18 | 12 | 230 |
| 19 | 24 | 390 |
| 20 | 63 | 25000 |
| 21 | 13 | 510 |
| 22 | 230 | |

Compounds of formula I ("the compounds"), originally identified as a Src inhibitor, are shown here to be a potent antiproliferative and proapoptotic agent against CML cells in culture. The apoptotic activity of the compounds against CML cells in culture is mirrored by its activity in vivo against CML xenografts. K562 tumors regress in nude mice when the compounds are administered p.o. once a day. The Abl-inhibitory activity of the compounds is likely a major contributor to the antiproliferative activity of the compounds against CML cells. Tyrosine phosphorylation of Bcr-Abl is eliminated at concentrations of the compounds greater than 100 nm, which alone should be sufficient to inhibit the proliferation and survival of Bcr-Abl-dependent myeloid cells.

Nude mice with K562 xenografts were examined on days 11, 22, 36, and 43. Data is presented as a ratio of animals lacking detectable tumors relative to the number of animals per group. K562 tumors imbedded in Matrigel were staged in nude mice until tumors reached 200-300 mm$^3$. The compound of example 1 was administered p.o. in 0.4% methocel/0.5% Tween at 75 mg/kg once a day for 5 days (8 mice/group).

TABLE 3

Tumor-free survival of mice with K562 xenografts receiving various oral doses of example 1 for 5 days

| | Day | | | |
|---|---|---|---|---|
| Dose | 11 | 22 | 36 | 43 |
| Vehicle | 0/6 | | | |
| 150 mg/kg | 8/8 | 8/8 | 8/8 | 8/8 |
| 100 mg/kg | 8/8 | 7/8 | 7/8 | 7/8 |
| 75 mg/kg | 7/8 | 6/8 | 6/8 | 6/8 |
| 50 mg/kg | 6/8 | 5/8 | 4/8 | 4/8 |

What is claimed is:

1. A pharmaceutical composition comprising a CML inhibiting amount of the compound 4-[(2,4-Dichloro-5-methoxyphenyl)amino]-6-methoxy-7-[3-(4-methyl-1-piperazinyl)propoxy]-3-quinolinecarbonitrile.

* * * * *